US009006192B2

(12) United States Patent
Tseng et al.

(10) Patent No.: US 9,006,192 B2
(45) Date of Patent: Apr. 14, 2015

(54) RNAI METHODS AND COMPOSITIONS FOR STIMULATING PROLIFERATION OF CELLS WITH ADHERENT JUNCTIONS

(75) Inventors: Scheffer Tseng, Pinecrest, FL (US); Wei Li, Guangdong (CN); Yingting Zhu, Miami, FL (US)

(73) Assignee: TissueTech, Inc., Miami, FL (US)

( * ) Notice: Subject to any disclaimer, the term of this patent is extended or adjusted under 35 U.S.C. 154(b) by 0 days.

(21) Appl. No.: 12/446,740

(22) PCT Filed: Sep. 27, 2007

(86) PCT No.: PCT/US2007/079757
§ 371 (c)(1),
(2), (4) Date: Jul. 21, 2009

(87) PCT Pub. No.: WO2008/103191
PCT Pub. Date: Aug. 28, 2008

(65) Prior Publication Data
US 2010/0003299 A1    Jan. 7, 2010

Related U.S. Application Data

(60) Provisional application No. 60/847,953, filed on Sep. 28, 2006.

(51) Int. Cl.
*A61K 48/00* (2006.01)
*C12N 5/079* (2010.01)
*A61K 31/00* (2006.01)
*A61K 35/44* (2006.01)
*A61K 38/16* (2006.01)
*C12N 15/113* (2010.01)

(52) U.S. Cl.
CPC .............. *C12N 5/0621* (2013.01); *A61K 31/00* (2013.01); *A61K 35/44* (2013.01); *A61K 38/164* (2013.01); *C12N 15/1138* (2013.01); *C12N 2310/14* (2013.01); *C12N 2501/58* (2013.01); *C12N 2509/00* (2013.01)

(58) Field of Classification Search
None
See application file for complete search history.

(56) References Cited

U.S. PATENT DOCUMENTS

| | | | |
|---|---|---|---|
| 2006/0147435 A1* | 7/2006 | Moon et al. | 424/93.21 |
| 2006/0292127 A1* | 12/2006 | Kulkarni et al. | 424/93.7 |
| 2009/0130108 A1* | 5/2009 | Reiter | 424/138.1 |
| 2009/0163432 A1 | 6/2009 | Takamatsu et al. | |

FOREIGN PATENT DOCUMENTS

| | | |
|---|---|---|
| WO | WO-01-06843 A2 | 2/2001 |
| WO | WO-2007-088372 A2 | 8/2007 |

OTHER PUBLICATIONS

Ghartey-Tagoe et al. (International J. Pharmaceutics 315 (2006) 122-133).*
Aho, S. et al., "Specific sequences in p120ctn determine subcellular distribution of its multiple isoforms involved in cellular adhesion of normal and malignant epithelial cells," J. Cell Sci. 115:1391-1402 (2002).
Brown et al., "Calcium modulation of adherens and tight junction function: a potential mechanism for blood-brain barrier disruption after stroke," Stroke 33:1706-1711 (2002).
Chen, et al., "Transplantation of adult human corneal endothileum ex vivo: a morphologic study," Cornea 20:731-737 (2001).
Chen, K.H. et al., "TGF-beta2 in aqueous humor suppresses S-phase entry in cultured corneal endothelial cells," Invest. Ophthalmol. Vis. Sci. 40:2513-2519 (1999).
Conacci-Sorrell et al., "Autoregulation of E-cadherin expression by cadherin-cadherin interactions: the roles of beta-catenin signaling, SLUG, and MAPK," J. Cell Biol. 163:847-857 (2003).
Daniel, J.M., "Dancing in and out of the nucleus: p120(ctn) and the transcription factor Kaiso," Biochim. Biophys. Acta 1773:59-68 (2007).
Davis, M. et al., "A core function ofr p120-catenin in cadherin turnover," J. Cell Biol. 163(3):525-534 (2003).
Engelmann, K. et al., "Prospects for endothelial transplantation," Exp. Eye Res. 78:573-578 (2004).
Fagotto, F. et al., "Cell contact-dependent signaling," Dev. Biol. 180:445-454 (1996).
Gavard, J. et al., "N-cadherin activation substitutes for the cell contact control in cell cycle arrest and myogenic differentiation: Involvement of p120 and beta-catenin," J. Biol. Chem. 279:36795-36802 (2004).
Gumbiner, B.M., "Regulation of cadherin adhesive activity," J. Cell Biol. 148:399-404 (2000).
Hartsock et al., "Adherens and tight junctions: structure, function and connections to the actin cytoskeleton," Biochim. Biophys. Acta 1778:660-669 (2008).
Hou, J.C. et al., "Dual regulation of Rho and Rac by p120 catenin controls adipocyte plasma membrane trafficking," J. Biol. Chem. 281:23307-23312 (2006).
Hsiue, G. et al., "A novel strategy for corneal endothelial reconstruction with a bioengineered cell sheet," Transplantation 81:473-476 (2006).

(Continued)

*Primary Examiner* — Kimberly Chong
(74) *Attorney, Agent, or Firm* — Wilson Sonsini Goodrich & Rosati

(57) ABSTRACT

Described herein are methods and compositions for stimulating proliferation of cells that express adherent junctions and cease proliferation, for example, human corneal endothelial cells, by downregulation of certain cell-cell junctions. In one embodiment, downregulation is achieved using RNA interference, and contacting the cells with mitogenic growth factors and an agent that elevates intracytoplasmic cAMP. Furthermore, described herein are methods of isolating human corneal endothelial cells from keratocytes, and methods of preserving and maintaining viability of human corneal endothelial cell aggregates. Also described are surgical grafts comprising human corneal endothelial cells that have been isolated, optionally stored, and transiently contacted with an agent that downregulates expression of p 120, and a biocompatible support. The methods and compositions described herein can be used in novel therapies to help expand human corneal endothelial cells during in vitro tissue engineering and for in vivo treatment of corneal endothelial dysfunction.

20 Claims, 4 Drawing Sheets

(56) References Cited

OTHER PUBLICATIONS

Ireton, R.C. et al., "A novel role for p120 catenin in E-cadherin function," J. Cell Biol. 159:465-476 (2002).
Ishino, Y. et al., "Amniotic membrane as a carrier for cultivated human corneal endothelial cell transplantation," Invest. Ophthalmol. Vis. Sci. 45:800-806 (2004).
Iyer, S. et al., "VE-cadherin-p120 interaction is required for maintenance of endothelial barrier function," Am. J. Physiol. Lung Cell Mol. Physiol. 286:L1143-1153 (2004).
Jamora, C. et al., "Intercellular adhesion, signalling and the cytoskeleton," Nat. Cell Biol. 4:E101-E108 (2002).
Joyce, N.C., "Proliferative capacity of the corneal endothelium," Prog. Retin. Eye Res. 22:359-389 (2003).
Joyce, N.C. et al., "Mechanisms of mitotic inhibition in corneal endothelium: contact inhibition and TGF-beta2," Invest. Ophthalmol. Vis. Sci. 43:2152-2159(2002).
Joyce, N.C. et al., "Mitotic inhibition of corneal endothelium in neonatal rats," Invest. Ophthalmol Vis. Sci. 30:2572-2583 (1998).
Joyce, N.C. et al., "Expression of cell cycle-associated proteins in human and rabbit corneal endothelium in situ," Invest. Ophthalmol. Vis. Sci. 37:1566-1575 (1996).
Kelly, K.F. et al., "NLS-dependent nuclear locatlization of p120ctn is necessary to relieve Kaiso-mediated transcriptional repression," J. Cell Sci. 117:2675-2686 (2004).
Kikuchi, M. et al., "p27kip1 siRNA induces proliferation in corneal endothelial cells from young but not older donors," Invest. Ophthalmol. Vis. Sci. 47:4803-4809 (2006).
Kim, T.Y. et al., "Differential activity of TGF-beta2 on the expression of p27Kip1 and Cdk4 in actively cycling and contact inhibited rabbit corneal endothelial cells," Mol. Vis. 7:261-270 (2001).
Kim, T.Y. et al., "Role of p27(Kip1) in cAMP-and TGF-beta2-mediated antiproliferation in rabbit corneal endothelial cells," Invest. Ophthalmol. Vis. Sci. 42:3142-3149 (2001).
Laing, R.A. et al., "Evidence for mitosis in the adult corneal endothelium," Ophthalmol. 91:1129-1134 (1984).
Lee, H. et al., "FGF-2 induced reorganization and disruption of actin cytoskeleton through PI 3-kinase, Rho, and Cde42 in corneal endothelial cells," Mol. Vis. 9:624-634 (2003).
Lee, H.T. et al., "Regulatory role of cAMP on expression of Cdk-4 and p27(Kip1) by inhibiting phosphatidylinositol 3-kinase in corneal endothelial cells," Invest. Ophthalmol. Vis. Sci. 44:3816-3825 (2003).
Li et al., "A novel method of isolation, preservation, and expansion of human corneal endothelial cells," Invest. Ophthalmol. Vis. Sci. 48:614-620 (2007).
Li et al., "The fate of limbal epithelial progenitor cells druing explant culture on intact amniotic membrane," Invest. Ophthalmol. Vis. Sci. 48:605-613 (2007).
Matter, K. et al., "Mammalian tight junctions in the regulation of epithelial differentiation and proliferation," Curr. Opin. Cell Biol. 17:453-458 (2005).
Mittal, V., "Improving the efficiency of RNA interference in mammals," Nature Reviews 5:355-365 (2004).
Mukoyama, Y. et al., "T-cadherin negatively regulates the proliferation of cutaneous squamous carcinoma cells," J. Invest. Dermatol. 124:833-838 (2005).
Nelson, W.J. et al., "Convergence of Wnt, beta-catenin, and cadherin pathways," Science 303:1483-1487 (2004).
Neufeld, A.H. et. al., "Maintenance of corneal endothelial cell shape by prostaglandin E2: effects of EGF and indomethacin," Invest. Ophthalmol. Vis. Sci. 27:1437-1442 (1986).
Park et al., "Kaiso/p120-catenin and TCF/beta-catenin complexes coordinately regulate canonical Wnt gene targets," Dev. Cell 8:843-854 (2005).
PCT/US07/79757 Search Report dated Aug. 28, 2008.
Perez-Moreno et al., "Sticky business: orchestrating cellular signals at adherens junctions," Cell 112:535-548 (2003).

Piedra et al., "p120 Catenin-associated Fer and Fyn tyrosine kinases regulate beta-catenin Tyr-142 phosphorylation and beta-catenin-alpha-catenin Interaction," Mol. Cell Biol. 23:2287-2297 (2003).
Pokutta, S. et al., "Structure and mechanism of cadherins and catenins in cell-cell contacts," Annu. Rev. Cell Dev. Biol. 23:237-261 (2007).
Roczniak-Ferguson et al., "Regulation of p120-catenin nucleocytoplasmic shuttling activity," J. Cell Sci. 116:4201-4212 (2003).
Rodova, M. et al., "Regulation of the rapsyn promoter by kaiso and delta-catenin," Mol. Cell. Biol. 24:7188-7196 (2004).
Roura et al., "Regulation of E-cadherin-Catenin association by tyrosine phosphorylation," J. Biol Chem. 274:36734-36740 (1999).
Senoo, T. et al., "EDTA: a promoter of proliferation in human corneal endothelium," Invest. Ophthalmol. Vis. Sci. 41:2930-2935 (2000).
Shapiro et al., "Structural basis of cell-cell adhesion by cadherins," Nature 374:327-337 (1995).
Spring et al., "The catenin p120ctn inhibits Kaiso-mediated transcriptional repression of the beta-catenin/TCF target gene matrilysin," Exp. Cell Res. 305:253-265 (2005).
Thoreson et al., "Selective uncoupling of p120(ctn) from E-cadherin disrupts strong adhesion," J. Cell Biol. 148:189-202 (2000).
Wildenberg, G.A. et al., "p120-catenin and p190RhoGAP regualte cell-cell adhesion by coordinating antagonism between Rac and Rho," Cell 127:1027-1039 (2006).
Willert, K. et al., "Beta-catenin: a key mediator of Wnt signaling," Curr. Opin. Genet. Dev. 8:95-102 (1998).
Yanagisawa et al., "A novel interaction between kinesin and p120 modulates p120 localization and function," J. Biol. Chem. 279:9512-9521 (2004).
Yoshida, K. et al., "Involvement of p27Kip1 in the proliferation of the developing corneal endothelium," Invest. Ophthalmol. Vis. Sci. 45:2163-2167 (2004).
Zhu, Y.T. et al., "Charcterization and comparison of intercellular adherent junctions expressed by human corneal endothelial cells in vivo and in vitro," Invest. Ophthalmol. Vis. Sci. 49:3879-3886 (2008).
Kawakita et al., "Intrasomal Invasion by Limbal Epithelial Cells Is Mediated by Epithelial-Mesenchymal Transition Activated by Air Exposure," Am J Path 167(2):381-392 (2005).
Davis et al., "A core function for p120-catenin in cadherin turnover," J Cell Biol 163(3):525-534 (2003).
Kikuchi et al., "p27kip1 siRNA induces proliferation in corneal endothelial cells from young but not older donors," Invest Ophthalmology Vis Sci 47(11):4803-4809 (2006).
Kuphal et al., "E-cadherin modulates Wnt-dependent transcription in colorectal cancer cells but does not alter Wnt-independent gene expression in fibroblasts," Exp Cell Res 312(4):457-467 (2006).
Lioni et al., "Dysregulation of claudin-7 leads to loss of E-cadherin esophageal squamous cell carcinoma cells," Am J Pathol 170(2):709-721 (2007).
Motti et al., "Reduced E-cadherin expression contributes to the loss of p27(kip1)-mediated mechanism of contact inhibition in thyroid anaplastic carcinoma," Carcinogenesis 26(6):1021-1034 (2005).
Qin et al., "The mammalian Scribble polarity protein regulates epithelial cell adhesion and migration through E-cadherin," J Cell Biol 171(6):1061-1071 (2005).
Rangwala et al., "Erbin regulates mitogen-activiated protein (MAP) kinase activation and MAP kinase-dependent interactions between Merlin and adherens junction protein complexes in Schwann cells," J Biol Chem 280(12):11790-11797 (2005).
Sheng et al., "Versican mediates mesenchymal-epithelial transition," Mol Biol Cell 17(4):2009-2020 (2006).
St-Croix et al., "E-cadherin-dependent growth suppression is mediated by the cyclin-dependent kinase inhibitor p27KIP1," J Cell Biol 142(2):557-571 (1998).
Zheng et al., "Analysis of metastasis suppressing function of E-cadherin in gastric cancer cells by RNAi," World J Gastroenterology 11(13):2000-2003 (2005).
EP 07873706 Supplementary Search Report and Written Opinion dated Nov. 5, 2010.

(56) References Cited

OTHER PUBLICATIONS

Kikuchi et al. "p27kip1 Antisense-induced proliferative activity of rat corneal endothelial cells." *Investigative Ophthalmology & Visual Science*, Jun. 2004, 45(6):1763-1770.

Lampugnani et al. "Contact Inhibition of VEGF-induced Proliferation Requires Vascular Endothelial Cadherin, β-catenin, and the Phosphatase DEP-1/CD148." *The Journal of Cell Biology*, 2003, vol. 161, No. 4, p. 120 (and see Table 6, Table 7).

CN200780043746.9 Second Office Action mailed Feb. 13, 2012.

EP07873706.1 Official Action mailed Dec. 16, 2011.

Luo, et al. "N-Cadherin Acts Upstream of VE-Cadherin in Controlling Vascular Morphogenesis." The Journal of Cell Biology, vol. 169 (1): 29-34 (2005).

Zhu, et al., "Nuclear p120 Cateinin Unlocks Mitotic Block of Contact-Inhibited Human Corneal Endothelial Monolayers without Disrupting Adherent Junctions," Journal of Cell Science 125(15):3636-3648 (2012).

Liu et al. "E-cadherin engagement stimulates proliferation via Rac1." *Journal of Cell Biology*, 2006, 173(3) : 431-441.

Japanese Patent Application No. 2009-530605 Office Action mailing date Jul. 31, 2012.

Engelmann, et al. Isolation and long-term cultivation of human corneal endothelial cells. Invest Ophthalmol Vis Sci. Nov. 1988;29(11):1656-62.

Joyce, et al. Human corneal endothelial cell proliferation: potential for use in regenerative medicine. Cornea. Nov. 2004;23(8 Suppl):S8-S19.

Kawakita, et al. Preservation and expansion of the primate keratocyte phenotype by downregulating TGF-beta signaling in a low-calcium, serum-free medium. Invest Ophthalmol Vis Sci. May 2006;47(5):1918-27.

Li, et al. A Novel Method of Isolation, Preservation, and Expansion of Human Corneal Endothelial Cells. Invest Ophthalmol Vis Sci. Feb. 2007; 48(2): 614--620. doi: 10.1167/iovs.06-1126.

PCT/US07/79757 written opinion dated Aug. 1, 2008.

\* cited by examiner

RNAi knockdown efficiency by real-time PCR quantitation of p120 mRNA using ARPE-19 cell line, Late Confluent (4 week culture)

SEQUENCE LISTING

<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gccagaggtg gttcggata                                                        19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tatccgaacc acctctggc                                                        19

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aacgaggtta tcgctgagaa c                                                     21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gttctcagcg ataacctcgt t                                                     21

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cagaggtgat cgccatgctt ggatt                                                 25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic

```
            oligonucleotide

<400> SEQUENCE: 6
aatccaagca tggcgatcac ctctg                                          25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gcgattgctt cgaaaggctc gtgat                                          25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
atcacgagcc tttcgaagca atcgc                                          25
```

RNAI METHODS AND COMPOSITIONS FOR STIMULATING PROLIFERATION OF CELLS WITH ADHERENT JUNCTIONS

GOVERNMENT SUPPORT

The invention was supported, in whole or in part, by grant number RO1 EY06819 and grant number RO1 EY015735 to Scheffer C. G. Tseng from National Eye Institute. The Government has certain rights in the invention.

CROSS-REFERENCE TO RELATED APPLICATIONS

The present application is filed pursuant to 35 U.S.C. §371 as a United States National Phase Application of International Application No. PCT/US2007/079757, filed Sep. 27, 2007, which claims the benefit of priority from U.S. Provisional Patent Application No. 60/847,953 filed Sep. 28, 2006, each of which applications is herein incorporated by reference in its entirety.

SEQUENCE LISTING

The instant application contains a Sequence Listing which has been submitted in ASCII format via EFS-Web and is hereby incorporated by reference in its entirety. Said ASCII copy, created on Sep. 30, 2010, is named 34157183.txt and is 2,219 bytes in size.

BACKGROUND OF THE INVENTION

An important refractive element of the eye, the cornea is the multi-layered, transparent, avascular, outermost part of the eye globe. For a human to see well, all layers of the cornea must remain transparent. Any cloudy or opaque area on a layer of the cornea will interfere with the proper refraction of light. The successive layers comprising the cornea, from the ocular surface inward, include the epithelium, Bowman's Layer, stroma, Descemet's membrane, and endothelium.

The human corneal endothelium, a single layer of cells lining the posterior surface of the cornea and facing the anterior chamber, plays a pivotal role in regulating corneal stromal hydration and hence, transparency. The human corneal endothelium has a critical fluid extraction or pumping function that is needed to maintain the transparency of the cornea. In a healthy eye, ocular fluid passes slowly from the interior to the stroma; and excess water is pumped from the stroma into the anterior chamber of the eye by the corneal endothelium. Further, it is critical that the rates of fluid moving into and out of the cornea are maintained in balance. If the pumping function of endothelial cells is diminished, the stroma would swell, and the regular pattern of the stroma's collagen matrix would be damaged by the excess water. This would result in the stroma becoming hazy, and eventually opaque.

SUMMARY OF THE INVENTION

Described herein are methods for stimulating the proliferation of cells with adherent junctions (AJs), comprising contacting the cells with an agent that downregulates expression of at least one cell-cell junction component. In one embodiment, the cell-cell junction component is an AJ protein or p190. In a further embodiment, the AJ protein is a cadherin. In yet a further embodiment, the cadherin is selected from N-cadherin, α-catenin, β-catenin, p120 catenin (hereafter abbreviated as p120), E-cadherin, VE-cadherin, and P-cadherin.

In one embodiment, the cells with AJs are, for example, endothelial cells, epithelial cells, smooth muscle cells, keratinocytes, ectodermal cells, or endodermal cells. In a further embodiment, the endothelial cells are, for example, human corneal endothelial cells (herein after abbreviated as HCECs; as used herein HCECs are the single layer of cells at the posterior surface of the cornea facing the anterior chamber), peritubular endothelial cells, brain microvessel endothelial cells, vascular endothelial cells, endothelial progenitor cells, vaginal epithelial cells, or any other type of epithelial cells. In yet a further embodiment, the epithelial cells are, for example, retinal pigment epithelial cells, myoepithelial cells, amniotic epithelial cells, urologic epithelial cells, breast epithelial cells, bronchial epithelial cells, ovarian epithelial cells, alveolar epithelial cells, or any other type of endothelial cells. In yet a further embodiment, the cells with AJs are HCECs.

In one embodiment, the agent is transiently contacted with the endothelial cells. In a further embodiment, the downregulation of the aforementioned components results from RNA interference. In yet a further embodiment, the RNA interference downregulates expression of p120. In yet a further embodiment, the agent is double stranded RNA. In yet a further embodiment, the RNA interference is applied in pulses.

In one embodiment, the cells are contacted with an agent in vivo, such as in the body of a mammal, for example, a human, monkey, dog, horse, cow, sheep, goat, pig, dog, cat, or rabbit. Preferably, the mammal is a human. In a further embodiment, the contacting occurs in the eye of a mammal. In yet a further embodiment, the eye of the mammal has a corneal endothelial dysfunction, such as, for example, bullous keratopathy (including aphakic or pseudophakic bullous keratopathy), corneal endothelial cell dystrophy (Fuchs' dystrophy), corneal edema, congenital hereditary endothelial dystrophy, or any other conditions where the corneal endothelium is damaged. In yet a further embodiment, the agent is administered to the anterior chamber of the eye of the mammal. In yet a further embodiment, the agent is administered directly into the anterior chamber of the eye.

In one embodiment, the cells are HCECs, and the agent is an agent that downregulates expression of N-cadherin, α-catenin, β-catenin, p120, and/or p190.

Further described herein are methods of expanding HCECs in culture comprising contacting the cells with an agent that downregulates expression of N-cadherin, α-catenin, β-catenin, p120, and/or p190; seeding the cells in a medium, for example, medium containing growth factors and/or agents that elevate intracytoplasmic cAMP; and culturing the cells to form expanded HCECs. In one embodiment, the agent is transiently contacted with the HCECs in aggregate or monolayer form. In a further embodiment, the downregulation of the aforementioned components results from RNA interference. In yet a further embodiment, the RNA interference downregulates expression of p120. In yet a further embodiment, the agent is double stranded RNA. In yet a further embodiment, the RNA interference is applied in pulses. In yet a further embodiment, the pulse of RNA interference lasts at least about 12 hours. In yet a further embodiment, the HCECs are in an aggregate state or in monolayer where AJs form.

In yet a further embodiment, the method of expanding HCECs described above further comprises contacting the cells with mitogenic growth factors. Mitogenic growth factors include, for example, epidermal growth factor (EGF), basic fibroblast growth factor (bFGF), other family members of FGF, hepatocyte growth factor, platelet-derived growth factor (PDGF), or interleukin-1 (IL-1). In yet a further embodiment, the method of expanding HCECs, of which the proliferation can be inhibited and AJ formation can be promoted by contacting the cells with an agent that elevates intracytoplasmic cAMP. Examples of agents that elevate intracytoplasmic cAMP include 8-bromo-cAMP, dibutyryl cAMP, isobutyl-methylxanthine, Pentoxifylline, forskolin, cholera toxin, prostaglandin E2 (PGE2), phenylbutyrate, Butaprost, Iloprost, or any other agent that elevates intracytoplasmic cAMP. In one particular embodiment, the agent that elevates intracytoplasmic cAMP is cholera toxin.

Further described herein are methods of isolating HCECs from keratocytes, comprising contacting a Descemet's membrane with a solution comprising collagenase, and separating the aggregates of HCECs from the solution after digestion. In one embodiment, the collagenase is collagenase A, collagenase B, collagenase D, or any enzyme that breaks triple helical peptide bonds in collagen. In another embodiment, the Descemet's membrane is contacted with a solution comprising collagenase for about 1 to about 18 hours for isolation of at least one HCEC aggregate, for example, from about 1.5 to about 17 hours, from about 5 to about 17 hours, from about 7 to about 17 hours, from about 10 to about 16 hours, from about 12 to about 16 hours, or any other time period from about 1 hour to about 18 hours. In one embodiment, aggregates of HCECs can be separated from the solution after digestion by pipetting. In another embodiment, aggregates of HCECs can be separated from the solution after digestion by centrifugation. In yet another embodiment, aggregates of HCECs can be separated from the solution after digestion by sieving through a cell sorter or mesh based on size.

Further described herein are methods of preserving and maintaining viability of HCEC aggregates comprising storing HCEC aggregates in a serum-free medium having a calcium ion concentration of about 0.8 mM to about 1.5 mM, for example, about 0.8 to about 1.5 mM, 0.85 mM to about 1.4 mM, about 0.9 mM to about 1.3 mM, about 0.95 mM to about 1.2 mM, about 1.0 mM to about 1.1 mM, or any other concentration from 0.8 mM to about 1.5 mM. In one embodiment, the calcium ion concentration is about 1.08 mM in storage medium. In a further embodiment, supplements are provided to the serum-free media.

Further described herein are surgical grafts comprising: HCECs that have been (a) isolated from keratocytes using a solution comprising collagenase, (b) optionally preserved in a serum-free medium having a calcium ion concentration of about 0.8 mM to about 1.5 mM, and (c) transiently contacted with an agent that downregulates expression of p120; and a biocompatible support. In one embodiment, the HCECs are further contacted with mitogenic growth factors. In another embodiment, AJ formation of the HCEC is further promoted by contact with an agent to elevate intracytoplasmic cAMP. In yet another embodiment, the HCECs are reseeded on the biocompatible support. The biocompatible support promotes HCEC adhesion, is transparent, and can be integrated to the corneal stroma. In one embodiment, the biocompatible support is a collagen-containing extracellular matrix. In another embodiment, the biocompatible support is an amniotic membrane. In a further embodiment, the thickness of the amniotic membrane has been decreased. In yet a further embodiment, the decrease in thickness has been achieved by means of excimer laser ablation. In yet a further embodiment, the agent is transiently contacted with the HCECs in aggregate or monolayer form. In a further embodiment, the agent that down-regulates expression of p120 is RNA interference. In yet a further embodiment, the agent is double stranded RNA. In yet a further embodiment, the RNA interference is applied in pulses.

DETAILED DESCRIPTION OF THE INVENTION

Figure 1:
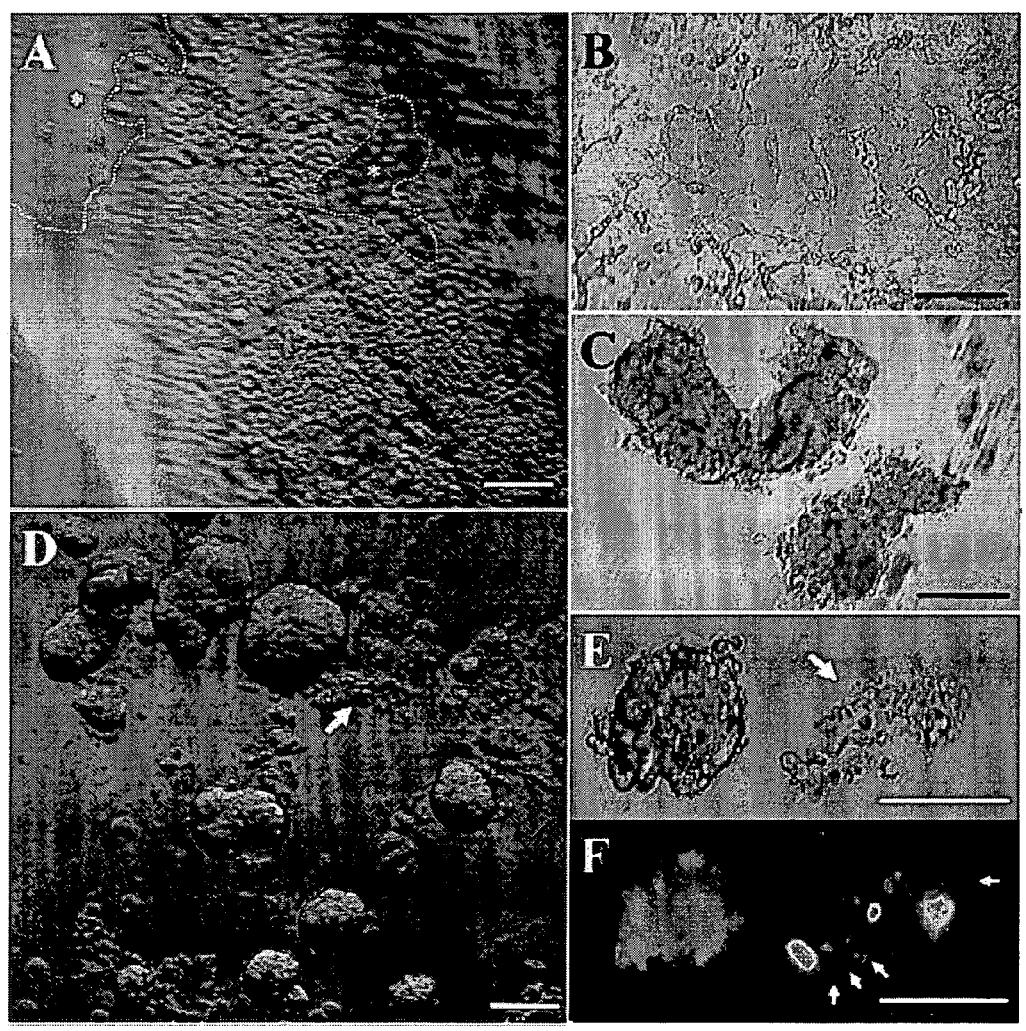
FIGS. 1A-F are illustrative micrographs of isolated HCECs as cell aggregates.

The appended claims particularly point out features set forth herein. A better understanding of the features and advantages of the present disclosure will be obtained by reference to the following detailed description that sets forth illustrative embodiments, in which the principles described herein are utilized.

Corneal endothelial cell density and endothelial cell function can decrease as a result of a number of diseases, trauma, or aging. Unlike other species such as rabbit and bovine, HCECs are notorious for their limited, insignificant regenerative capacity and proliferative capacity in vivo. The damaged or destroyed HCECs are not regenerated by the individual.

Destruction and/or dysfunction of HCECs can progress to corneal edema or bullous keratopathy, which then causes loss of vision. An example of a disease in which a deterioration of HCECs occurs is corneal endothelial cell dystrophy, also known as Fuchs' dystrophy. Trauma and damage to the corneal endothelium can also result from injury, cataract surgery, or radial keratotomy.

About 30 percent of all corneal transplantations are performed because of corneal endothelium diseases. Presently, corneal transplantation of full or partial thickness of a cadaver donor cornea containing a healthy corneal endothelium is the only available remedy for loss of sight due to damaged or diseased corneal endothelium. However, due to the increasing risk of transmissible diseases, and the widespread use of corrective eye surgery which renders corneas unsuitable as replacement tissue, there is a shortage of suitable donor corneal tissue. Furthermore, long-term preservation of corneal tissue for use as donor tissue remains an unsolved problem.

The major means of replenishing the loss of HCECs in vivo due to the occurrence of dystrophy, trauma and surgical intervention is compensatory cell migration and enlargement. As an alternative therapy for corneal endothelial dysfunction, described herein are methods for stimulating proliferation of cells that form AJs during differentiation and thus lose proliferative potential, such as HCECs, by contacting the cells with an agent that downregulates expression of E-cadherin, VE-cadherin, P-cadherin, N-cadherin, α-catenin, β-catenin, p120, and/or p190.

Further, manipulation of HCEC's proliferation can help expand HCECs to treat eyes with dysfunctional HCECs as a strategy for in vivo therapies and in vitro tissue engineering. The ability to engineer the human corneal endothelium in vitro is important, because it may then avoid the necessity of having surgical transplantation of the cornea or HCECs, and such tissue may also be used as an alternative graft to restore vision in eyes inflicted with corneal endothelial failure. Accordingly, described herein are methods of isolation, preservation, and expansion of HCECs by stimulation of proliferation intermittently (with a pulse mode), interspersed or intermixed with mitogenic stimuli and agents elevating intracytoplasmic cAMP and promoting differentiation with AJ reformation, and a new surgical graft to replace corneal endothelial tissues.

In theory, an effective engineering method should comprise three key steps: isolation of HCECs from a donor cornea, preservation of isolated HCECs for a period of time in order to allow for transportation, and expansion of isolated HCECs on an appropriate in vitro environment suitable for transplantation. In each of these steps, HCECs could also be influenced by the medium to which the cells are exposed that may influence the balancing acts between AJ formation and cellular proliferation.

A prerequisite for tissue engineering of the human corneal endothelium is to ensure effective isolation, preservation and expansion from a small number of HCECs. Another prerequisite is to ensure proliferation (expansion) is not coupled with the loss of the normal HCEC phenotype, but rather with the maintenance (restoration) of HCEC phenotype with AJ formation.

Methods of Isolation

Disclosed herein are methods for isolating HCECs from being contaminated by adjacent stromal keratocytes. Mechanically stripped Descemet's membranes contain some stromal tissue, in which there are keratocytes. Previous methods employed EDTA with or without trypsin, dispase with or without subsequent trypsin/EDTA, trypsin or EDTA followed by collagenase, or collagenase followed by trypsin or EDTA. However, these methods led to cellular degeneration because of prolonged incubation time needed to detach cells from the matrix, cell damage and decreased yield, or fibroblast (keratocyte) contamination. Further, these methods required use of additional selective medium to prevent such fibroblast (keratocyte) contamination from occurring.

The methods disclosed herein include the steps of, e.g., contacting a Descemet's membrane with a solution comprising collagenase, and separating the HCEC aggregates from the solution. For example, the Descemet's membrane can be digested in a solution comprising a concentration of collagenase for a period of time sufficient for the adherent HCECs to detach from the dissolved membrane and form at least one aggregate of HCECs suspended in the solution without keratocytes, which are excluded from the aggregate. Digestion in collagenase solution helps to eliminate contamination of keratocytes from the corneal stroma because formed HCEC aggregates can then be transferred to a separate culture dish to avoid contamination of keratocytes. Such HCEC aggregates should retain cell-matrix interactions and cell-cell AJs, similar to the in vivo state.

The collagenase used may be, for example, collagenase A, collagenase B, collagenase D, or any enzyme that breaks peptide bonds in collagen. The concentration of collagenase A in the solution can range from, about 0.5 mg/ml to about 5 mg/ml, e.g., about 0.75 mg/ml to about 4 mg/ml, about 1 mg/ml to about 3 mg/ml, about 1 mg/ml to about 2 mg/ml, about 1.5 mg/ml to about 2.0 mg/ml, or any other range from about 0.5 mg/ml to about 5 mg/ml.

The solution to isolate at least one aggregate of HCECs from keratocytes can comprise any culture medium suitable for culturing such cells, such as supplemented hormonal epithelial medium (SHEM). The culture medium can be supplemented with other materials such as, e.g., serum, antibiotics, growth factors, or agents to elevate intracytoplasmic cAMP. Agents that can be used to elevate intracytoplasmic cAMP include, for example, membrane permeable cAMP analogues such as 8-bromo-cAMP and dibutyryl cAMP, and other intracellular cAMP-elevating agents such as the phosphodiesterase inhibitor, e.g., isobutyl-methylxanthine and Pentoxifylline, the adenylate cyclase activator such as forskolin or cholera toxin, or exogenous agents such as prostaglandin E2 (PGE2), phenylbutyrate, Butaprost, or Iloprost, or any other agent that elevates intracytoplasmic cAMP. In one embodiment, the culture medium comprises an equal volume of HEPES-buffered DMEM and HAM's F12; 5% Fetal Bovine Serum; 0.5% dimethyl sulfoxide; 2 ng/ml mouse Epidermal Growth Factor; 5 µg/mL insulin; 5 µg/ml transferrin; 5 ng/ml selenium; 0.5 µg/ml hydrocortisone; 1 nM cholera toxin; 50 µg/ml gentamicin; and 1.25 µg/ml amphotericin B.

The Descemet's membrane can be incubated at a temperature of about 37° Celsius for about 1 to about 18 hours for isolation of at least one HCEC aggregate from keratocytes, for example, from about 1.5 to about 17 hours, from about 5 to about 17 hours, from about 7 to about 17 hours, from about 10 to about 16 hours, from about 12 to about 16 hours, or any other time period from about 1 hour to about 18 hours. The time of incubation in collagenase solution necessary to isolate HCECs can depend on, e.g., the amount of digestion desired, the number of HCEC aggregates desired, the concentration of collagenase solution, and/or the size of the Descemet's membrane to be digested, and, based on the disclosures provided herein, can be readily determined by one of ordinary skill in the art.

Following digestion of the Descemet's membrane and isolation of the HCEC aggregates from keratocytes, aggregates can be collected and removed from the solution by pipetting. Alternatively, the HCEC aggregates can be collected by other methods, including centrifugation or sieving through a cell sorter or mesh based on size. In any event, collection should occur without disrupting the aggregates.

Methods of Preserving/Maintaining

Figure 2:
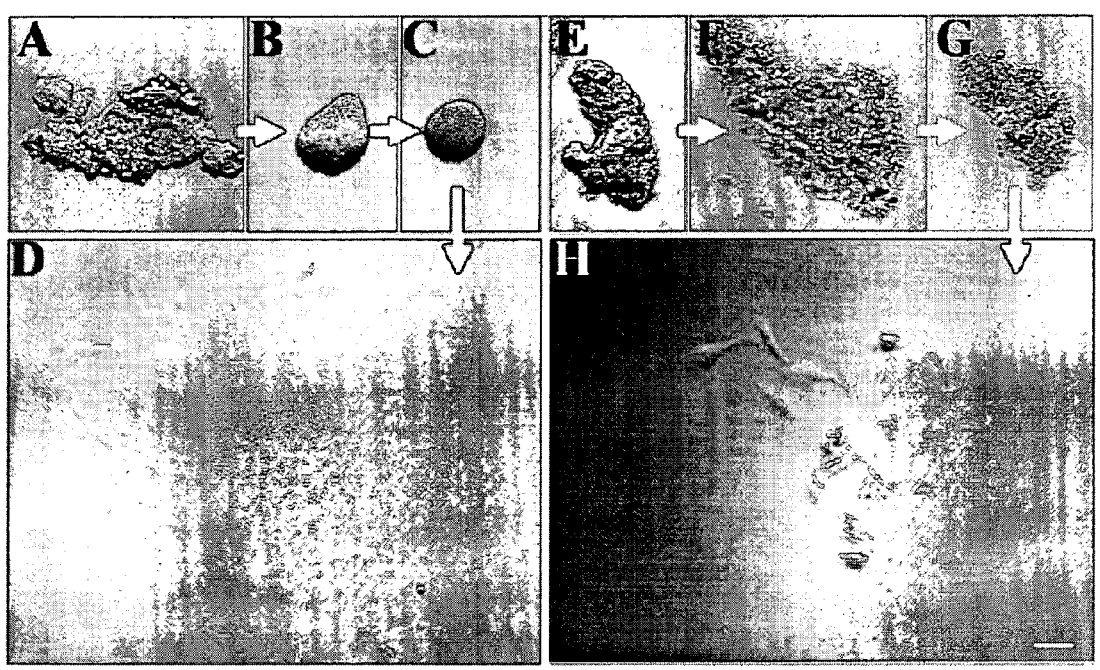
FIG. 2A and FIG. 2E are illustrative micrographs showing HCEC aggregates harvested from collagenase A digestion.
FIG. 2B and FIG. 2C are illustrative micrographs showing HCEC aggregates from FIG. 2A in a high calcium serum-free medium.
FIG. 2F and FIG. 2G are illustrative micrographs showing HCEC aggregates from FIG. 2E in a low calcium serum-free medium.
FIG. 2D is an illustrative micrograph showing the intact human corneal endothelial monolayer obtained by further culturing HCEC aggregates shown in FIG. 2C in SHEM.
FIG. 2H is an illustrative micrograph showing scattered single cells generated by further culturing HCEC aggregates shown in FIG. 2G in a low calcium serum-free medium.

Isolated HCEC aggregates, including those isolated as described above, can further be organized into round spheres if continuously cultured in serum-free high calcium concentration medium for up to about 3 weeks or longer, and that such preserved spheres could yield a monolayer of HCECs with a phenotypic hexagonal shape (FIG. 2D). Disclosed herein are methods of preserving and maintaining viability of HCEC aggregates by storing the aggregates in a serum-free medium having a high calcium ion concentration.

As used herein, a high calcium ion concentration is about 0.8 mM to about 1.5 mM calcium concentration in storage medium, for example, about 0.8 to about 1.5 mM, 0.85 mM to about 1.4 mM, about 0.9 mM to about 1.3 mM, about 0.95 mM to about 1.2 mM, about 1.0 mM to about 1.1 mM, or any other concentration from 0.8 mM to about 1.5 mM. In one embodiment, the calcium ion concentration is about 1.08 mM in storage medium.

The storage medium can be any serum-free medium appropriate for storing HCECs, for example, Dulbecco's modified Eagle's medium (DMEM), Ham's F12, or a mixture of DMEM and F12 as used in SHEM, so long as the calcium concentrations meet the above criteria. In the medium, additional growth supplements can be added such as mitogenic growth factors, antibiotics, agents to elevate intracytoplasmic cAMP, KSFM supplements, or SHEM supplements so long as fetal bovine serum (FBS) or other serum factors including fibronectin is eliminated.

Once the HCEC aggregates are placed in the serum-free, high calcium concentration storage medium, they can be incubated in, e.g., a tissue culture incubator, at a temperature of e.g., about 37° Celsius for up to about 3 weeks or longer. The aggregates can remain as floating aggregates in the storage medium, and can be used for subsequent cultivation in, e.g., serum-containing medium, as described below. Further, proliferation of the HCEC aggregates may be stimulated as described below.

Methods of Expansion

Disclosed herein are methods of stimulating proliferating cells that form AJs during differentiation and cease proliferation, comprising contacting the cells with an agent that downregulates expression of E-cadherin, VE-cadherin, P-cadherin, N-cadherin, α-catenin, β-catenin, p120, and p190. For example, proliferation of HCEC aggregates isolated and preserved or HCEC monolayers derived from HCEC aggregates as described above can be stimulated using the described methods.

Not wishing to be bound by theory, it is proposed that disruption of cell-cell junctions of HCECs may help them spread as a monolayer for expansion. Cell-cell contacts include AJs, tight junctions (TJ), and desmosomes. Among these contacts, AJs are particularly important in controlling cell proliferation, communication, specificity, formation and maintenance of intercellular adhesion. AJs are actin-based intercellular junctions mediated by cadherins and catenins, and represent a distinct family of single transmembrane domain glycoproteins that mediate calcium-dependent cell proliferation and cell-cell adhesion. The key members of AJs include cadherins, α-catenin, β-catenin and p120. Among the cadherin family, there are E-cadherin, VE-cadherin, N-cadherin and P-cadherin, the expression of which depends on cell type. In general, catenins are a family of 80 to 102-kilodalton proteins that are thought to have a major role in regulation of cell-to-cell adhesion, related to their interaction with E-cadherin, other cadherins and the actin cytoskeleton. P190 is a RhoA family GTPase activating protein that regulates actin stress fiber dynamics, and plays a role in regulating cytoskeletal dynamics by inhibiting focal adhesions and myosin-mediated contraction of F-actin cables.

For HCECs, the key adherin is N-cadherin but not E-cadherin or VE-cadherin (which are produced in much smaller amounts); as described herein, α-catenin, β-catenin, p120 and p190 are also present in HCECs. Classically, cell-cell junctions have been regarded as structural elements of differentiated cells. However, not wishing to be bound by theory, unlocking the mitotic block of HCECs by transient downregulation of these cell-cell junction components can facilitate expansion of HCECs. N-cadherin, α-catenin, β-catenin, p120 and p190 are thus appropriate targets for unlocking the mitotic block in HCECs.

Previous methods for stimulating proliferation of cells with AJs employed enzymes such as trypsin and/or divalent cation-chelating agents such as EDTA. However, methods employing trypsin/EDTA cannot be used effectively in in vivo applications because it is potentially hazardous. Further, trypsin/EDTA may dissociate the surrounding cell-matrix interactions, and additionally targets more than one component of AJs. In addition, trypsin/EDTA will dissociate HCECs and adjacent keratocytes indiscriminately. Following such non-specific and broad dissociation of cell-cell junction and cell-matrix interactions, HCECs will proliferate but also transform into fibroblasts, mimicking a pathological state termed retrocorneal membrane, especially under the stimulation by growth factors such as IL-1 and bFGF.

In one embodiment, a brief EDTA treatment promoted proliferation of HCEC aggregates by releasing mitotic block mediated by cell-cell contacts (Example 3). However, as described above, such a treatment produced HCEC cells that were inappropriate for human transplantation, and resulted in non-specific and broad dissociation of cell-cell junction and cell-matrix interactions.

Figure 4:
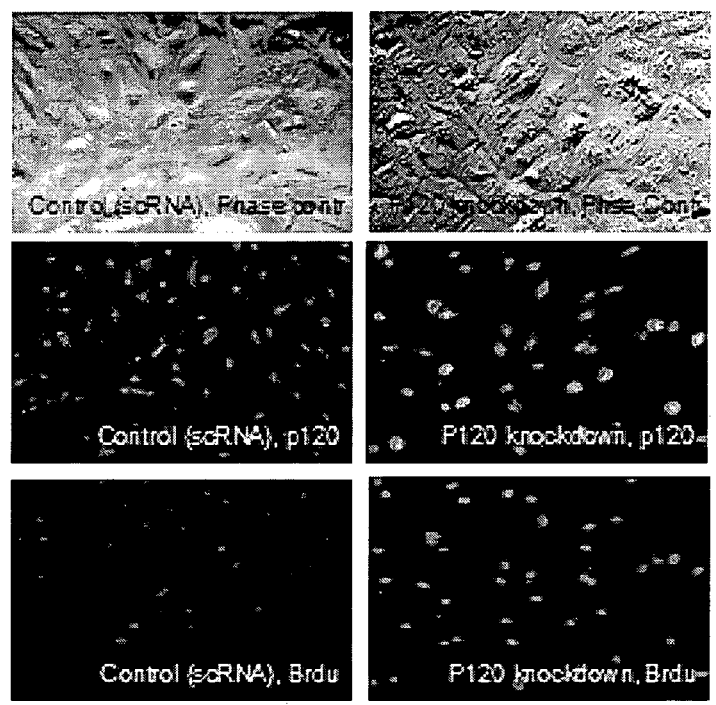
FIG. 4 is an illustrative photograph showing control (scRNA) and p120 RNAi I knockdown cultures, demonstrating translocalization of p120 to each nucleus of cells, which also shows proliferation judged by nuclear staining of BrdU.

In another embodiment, proliferation of cells with AJs can be stimulated by targeting specific cell-cell junction components. Cell-cell junction components may be knocked down to facilitate unlock of the mitotic block of cells expressing AJs during differentiation at the same time as loss of the proliferative potential. Examples of cadherins include E-cadherins, VE-cadherins, N-cadherins, and P-cadherins. Examples of catenins include α-, β-, γ-catenin and p120. If the RNAi to be knocked down is p120, for example, p120 RNAi 1 or p120 RNAi 3 can be used (Table 5). Downregulation of p120 leads to dissolution of cell-cell junctions with marked downregulation of E-cadherin, VE-cadherin, and β-catenin for ARPE-19 cells (Example 5) and N-cadherin, E-cadherin, VE-cadherin, and β-catenin for HCECs (Example 6). Furthermore, p120 was translocated from the cell-cell junction to the nucleus in HCECs, which demonstrate proliferation as judged by nuclear staining to BrdU (a label signifying DNA synthesis) (FIG. 4). Cadherins (i.e., N-cadherin for HCECs), α-catenin and β-catenin were found to be metabolically unstable when cell-cell junctions were perturbed while p120 was not (Example 4, Table 3), indicating that targeting of p120 was specific and more effective.

In another embodiment, proliferation of cells with AJs can be stimulated by targeting p120 by RNAi knockdown. RNAi refers to the introduction of double stranded RNA (dsRNA) into a cell, where it induces the degradation of complimentary mRNA and thereby suppresses gene expression. Published RNAi sequences may be used to downregulate p120, or specific RNAi sequences can be designed, e.g., based on Invitrogen Blockit™ RNAi Designer by considering, for example, (a) different target regions of the desired mRNA open reading frame; (b) RNAi design principles as published in Mittal V, Nature (2004) 5:355-365; and (c) BLAST searches to ensure that the desired RNAi are specific.

For in vivo applications, RNAi can be applied in pulses, e.g., RNAi is applied for a period followed by a withdrawal, during which time medium containing mitogenic stimuli together with or followed by agents elevating intracytoplasmic cAMP is applied for a period before the next application of RNAi. For example, RNAi can be applied for about 12 to about 72 hours, e.g., about 12 hours, about 16 hours, about 20 hours, about 24 hours, about 28 hours, about 32 hours, about 36 hours, about 40 hours, about 44 hours, about 48 hours, about 52 hours, about 56 hours, about 60 hours, about 64 hours, about 68 hours, about 72 hours, or any other time in between about 12 to about 72 hours, and the withdrawal or resting period can be for any time period for about 12 to about 48 hours, e.g., about 12 hours, about 16 hours, about 20 hours, about 24 hours, about 28 hours, about 32 hours, about 36 hours, about 40 hours, about 44 hours, about 48 hours, about 52 hours, about 56 hours, about 60 hours, about 64 hours, about 68 hours, about 72 hours, or any other time in between about 12 to about 72 hours. In one embodiment, RNAi is applied for a period of 24 hours and then followed by a withdrawal or resting period of 24 hours before the next pulse application of RNAi is performed.

In one embodiment, the cells are contacted with an agent in vivo, such as in the body of a mammal, for example, a horse, cow, sheep, goat, pig, dog, cat, rabbit, monkey, or human. Preferably, the mammal is a human. In a further embodiment, the contacting occurs in the eye of a mammal. In yet a further embodiment, the eye of the mammal has a corneal endothelial dysfunction, such as, for example, bullous keratopathy (including aphakic or pseudophakic bullous keratopathy), corneal endothelial cell dystrophy (Fuchs' dystrophy), corneal edema, congenital hereditary endothelial dystrophy, or any condition where the corneal endothelium is damaged. In yet a further embodiment, the agent is administered to the anterior chamber of the eye of the mammal.

For in vitro applications, RNAi can be applied to cultures of HCECs in aggregate or monolayer form in pulses and interspersed or intermixed with replacement of a medium containing mitogenic stimuli together with or followed by agents elevating intracytoplasmic cAMP, e.g., RNAi is applied for a period and then followed by a withdrawal or resting period with fresh culture medium which contains mitogenic stimuli together with or followed by agents elevating intracytoplasmic cAMP before the next pulse application of RNAi. For example, RNAi can be applied for about 12 to about 72 hours, e.g., about 12 hours, about 16 hours, about 20 hours, about 24 hours, about 28 hours, about 32 hours, about 36 hours, about 40 hours, about 44 hours, about 48 hours, about 52 hours, about 56 hours, about 60 hours, about 64 hours, about 68 hours, about 72 hours, or any other time in between about 12 to about 72 hours, and the withdrawal or resting period can be for any time period for about 12 to about 48 hours, e.g., about 12 hours, about 16 hours, about 20 hours, about 24 hours, about 28 hours, about 32 hours, about 36 hours, about 40 hours, about 44 hours, about 48 hours, about 52 hours, about 56 hours, about 60 hours, about 64 hours, about 68 hours, about 72 hours, or any other time in between about 12 to about 72 hours. The fresh culture medium applied during the withdrawal or resting period can be any culture medium suitable for culturing such cells, such as supplemented hormonal epithelial medium (SHEM). In one embodiment, RNAi is applied for a period mentioned above before being replaced by a medium containing mitogenic stimuli, e.g., using peptide growth factors such as EGF and bFGF, together with or followed by agents elevating intracytoplasmic cAMP, e.g., cholera toxin, to promote AJ formation for 24 hours or any period of time mentioned above, before the next pulse application of RNAi is performed.

The HCEC culture to which RNAi is to be applied can be either in aggregate or monolayer form. HCEC monolayers can be either early confluent (e.g., confluent for about 1, about 2, about 3, about 4, about 5, about 6, or about 7 days confluent), or late confluent (e.g., about 2 weeks, about 3 weeks, about 4 weeks, or about 5 weeks confluent). Following RNAi transient transfection of HCEC cells, the transfection reagents can be removed and the cells can be passaged and expanded according to cell culture techniques as described above, to maintain characteristic hexagonal mosaic phenotype.

In a further embodiment, the culture medium applied to the HCECs is supplemented with agents that may elevate intracytoplasmic cAMP. Without wishing to be bound by theory, elevation of intracytoplasmic cAMP counteracts undesired side effects caused by prolonged and persistent proliferation caused by mitogenic growth factors such as EGF or bFGF, especially IL-1 and bFGF, such as transformation into fibroblasts and loss of the characteristic HCEC phenotype. Agents that can be used to elevate intracytoplasmic cAMP include, for example, membrane permeable cAMP analogues such as 8-bromo-cAMP and dibutyryl cAMP, and other intracellular cAMP-elevating agents such as the phosphodiesterase inhibitor, e.g., isobutyl-methylxanthine and Pentoxifylline, the adenylate cyclase activator such as forskolin or cholera toxin, or exogenous agents such as prostaglandin E2 (PGE2), phenylbutyrate, Butaprost, or Iloprost, or any other agent that elevates intracytoplasmic cAMP. The resulting cells are appropriate for human transplantation.

Surgical Grafts/Methods of Treatment

HCECs prepared as described above can be delivered as a tissue with or without appropriate carriers or supports, i.e., as a surgical graft. Disclosed herein are surgical grafts comprising HCECs that have been (a) isolated from keratocytes using a solution comprising collagenase, (b) optionally preserved in a serum-free medium having a calcium ion concentration of about 0.8 mM to about 1.5 mM, and (c) transiently contacted with an agent that downregulates expression of p120; and a biocompatible support. In one embodiment, the HCECs are further contacted with mitogenic growth factors. In another embodiment, AJ formation of the HCEC is further promoted by contact with an agent to elevate intracytoplasmic cAMP. In yet another embodiment, the HCECs are reseeded on the biocompatible support. The biocompatible support promotes HCEC adhesion, is transparent, and can be integrated to the corneal stroma. In one embodiment, the biocompatible support is a collagen-containing extracellular matrix. In another embodiment, the biocompatible support is an amniotic membrane. In a further embodiment, the thickness of the amniotic membrane has been decreased. In yet a further embodiment, the decrease in thickness has been achieved by means of excimer laser ablation. In yet a further embodiment, the agent is transiently contacted with the HCECs in aggregate or monolayer form. In a further embodiment, the agent that downregulates expression of p120 is RNA interference. In yet a further embodiment, the agent is double stranded RNA. In yet a further embodiment, the RNA interference is applied in pulses.

The HCEC source for such a graft can be derived from either an autologous (from the same individual) or allogeneic (from a different individual) source, and used as a surgical graft to treat patients with corneal endothelial diseases. An autograft is a graft prepared from the recipient's own tissue, for example from a healthy eye of the recipient. An allograft is a graft of tissue between individuals who are not genetically identical. An allograft may be prepared from tissue obtained from a cadaveric eye or living-related individual, for example. An autograft presents the advantage of avoiding allograft rejection, which cannot be avoided in conventional corneal transplantation.

In addition, HCECs prepared as described above can also be included to engineer or regenerate tissues, such as the corneal stroma or the entire corneal tissue. Such engineered tissues can be used as a surgical graft, and for purposes of testing for therapies or to be incorporated with gene therapies to augment the function of the tissue. The methods and compositions described herein may also be expanded to other species for the same applications.

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Reference thereto evidences the availability and public dissemination of such information.

Example 1

Isolation of HCECs

Materials: Dulbecco's modified Eagle's medium (DMEM), Ham's/F12 medium, keratinocyte serum-free medium (KSFM), OptiMEM-1 medium, HEPES buffer, Hank's balanced salt solution (HBSS), phosphate-buffered saline (PBS), amphotericin B, gentamicin, fetal bovine serum (FBS), bovine pituitary extract, human recombinant epidermal growth factor (h-EGF), 0.25% trypsin/0.53 mM EDTA (trypsin/EDTA), and LIVE/DEAD assay reagent were purchased from Invitrogen (Carlsbad, Calif.). Dispase II and collagenase A were obtained from Roche (Indianapolis, Ind.). Hydrocortisone, dimethyl sulfoxide, cholera toxin, insulin-transferrin-sodium selenite media supplement, L-ascorbic acid, chondroitin sulfate, propidium iodide, Hoechst-33342 dye, Triton X-100, bovine serum albumin (BSA), human basic fibroblast growth factor (h-bFGF), paraformaldehyde, and FITC conjugated anti-mouse IgG were from Sigma (St. Louis, Mo.). Mouse anti-ZO-1 antibody and Type I collagen were from BD Biosciences (Bedford, Mass.). Mouse anti-laminin 5, type IV collagen $\alpha 2$ chain, perlecan, and connexin 43 antibodies were from Chemicon (Temecula, Calif.). Mouse anti-type IV collagen $\alpha 1$ antibody was from Kamiya Biomedical (Seattle, Wash.). Anti-fade mounting solution was from Vector Laboratories (Burlingame, Calif.). Mouse anti-Ki67 antibody was from DakoCytomation (Carpinteria, Calif.). DeadEnd™ fluorometric TUNEL system was from Promega (Madison, Wis.).

Human tissue was handled according to the Declaration of Helsinki. Eighteen corneoscleral tissues from human donor eyes were obtained from the Florida Lions Eye Bank (Miami, Fla.), some of their central corneal buttons had been used for corneal transplantation. The donors' ages were between 18 to 68 years (41.4±15.8 years). All tissues were maintained at 4° C. in the OPTISOL® (Bausch & Lomb, New York) medium for less than 10 days before study. The tissue was rinsed three times with DMEM medium containing 50 mg/mL gentamicin and 1.25 mg/mL amphotericin B.

The central cornea was removed by a trephine of 8 mm diameter. Afterwards, the Descemet's membrane as well as corneal endothelial cells were stripped from the posterior surface of the peripheral corneoscleral tissue under a dissecting microscope and digested at 37° C. for 1.5 to 16 hours with 2 mg/mL collagenase A in SHEM medium, which was made of an equal volume of HEPES-buffered DMEM and Ham's F12 supplemented with 5% FBS, 0.5% dimethyl sulfoxide, 2 ng/mL mouse EGF, 5 µg/mL insulin, 5 µg/mL transferrin, 5 µg/mL selenium, 0.5 µg/mL hydrocortisone, 1 nM cholera toxin, 50 µg/mL gentamicin, and 1.25 µg/mL amphotericin B. After digestion, HCECs formed aggregates, which were collected by centrifugation at 2,000 rpm for 3 minutes to remove the digestion solution. As a control, Descemet's membrane strips were also digested in 10 mg/ml dispase II in SHEM medium and trypsin/EDTA for up to 3 hours.

Collagenase digestion for 1.5 hours was sufficient to separate endothelial cells from Descemet's membrane and form loose aggregates, leaving denuded Descemet's membrane behind. After 3 hours digestion, endothelial cell aggregates derived from collagenase digestion became more compact; however, Descemet's membrane had not yet dissolved. After 12 hours digestion, Descemet's membrane was completely digested, and the majority of the HCEC aggregates became very compact. In these HCEC aggregates endothelial cells kept high viability, as confirmed by LIVE/DEAD assay and TUNEL assay. Those few HCEC aggregates kept loose were proved to have contained more dead cells. Based on these results, we concluded that 12 hours digestion resulted in compact HCEC aggregates with high cell viability. These compact HCEC aggregates may facilitate long term preservation of endothelial cells because they maintained cell-cell junctions.

Results. After the Descemet's membrane was surgically stripped off from the peripheral cornea of the corneoscleral ring tissue, the majority of HCECs still adhered to the Descemet's membrane, while some cells detached (marked by dotted lines and asterisks), creating regions without cells (FIG. 1A). After dispase II digestion at 37° C. for 1.5 hour in SHEM, HCECs started to aggregate but still did not detach from the Descemet's membrane (FIG. 1B).

In contrast, after the stripped Descemet's membrane was digested in collagenase A for 1.5 hour, HCECs aggregated into considerable clusters and completely detached from the Descemet's membrane (FIG. 1C), leaving an intact Descemet's membrane behind. After three hours, such aggregates derived from collagenase A digestion became more compact. However, cells still did not detach from the Descemet's membrane and started to disintegrate following dispase II digestion (data not shown). Notably, after 16 hours of collagenase A digestion, the Descemet's membrane was dissolved and most HCEC aggregates were compact and exhibited different sizes and shapes (FIG. 1D), while very few demonstrated looseness (FIG. 1D, 1E, arrows).

The LIVE/DEAD assay showed that the compact aggregates were composed of viable cells exhibiting intense green fluorescence (FIG. 1F). In contrast, loosened aggregates contained dead cells (FIG. 1F, marked by arrows). FIG. 1E is the phase contrast micrograph of FIG. 1F. Bars represent 100 micrometers (µm). We speculated that these cells may have already been dead during storage of the donor cornea, and thus were unable to form aggregation during collagenase A digestion.

To investigate whether cell-cell junctions and basement membrane components were still maintained after collagenase A digestion, HCEC aggregates were embedded in OCT, prepared for cryosections, and subjected to immunostaining. The results showed that tight junction ZO-1, gap junction connexin-43, and such basement membrane components as type IV collagen $\alpha 1$ and $\alpha 2$ chains, laminin 5, and perlecan were all present in HCEC aggregates.

Nuclear counterstaining further showed that HCECs in the aggregate were compact. The TUNEL assay confirmed that only few apoptotic cells were present in the center of the aggregate.

To further investigate whether these basement membrane components helped to maintain the viability of HCECs, collagenase-isolated aggregates were subsequently treated with dispase II (10 mg/mL in SHEM) at 4° C. for 16 hours, a treatment as we have reported that can remove collagen IV and laminin 5. The results showed that the additional dispase II digestion did not disintegrate HCEC aggregates, and that the cells within were still alive, as judged by the Live and Dead assay. However, dispase-treated HCEC aggregates could not readily attach on plastic in SHEM whereas dispase non-treated aggregates could. These results indicated that cell-cell junctions might play a more important role in forming the aggregate and maintaining the cell viability of HCECs than cell-matrix interactions, and that the remaining basement membrane matrix components in aggregates might play an important role in facilitating cell attachment of HCECs on plastic during subculturing.

Example 2

Preservation of Isolated HCEC Aggregates

The resultant HCEC aggregates were preserved in a serum-free low calcium or high calcium medium with different supplements (Table 1). The calcium concentration of storage medium 1, a KSFM-based medium, is 0.08 millimolar (mM), which we defined as "low calcium" medium. The calcium concentration of storage medium 2, 3, and all the culture media is about 1.08 mM, based on the basal medium of DMEM.F12 and the calcium in FBS. We defined these media having a calcium concentration of about 1.08 millimolar (mM) as "high calcium" media.

HCEC aggregates were stored in a tissue culture incubator at about 37° C. for up to 3 weeks. Cell viability was determined by Live and Dead assay, and also evaluated by subculturing them in a serum-containing medium (Table 2).

TABLE 1

Different Storage Media for HCEC Aggregates

| Medium Type | Basal medium | Supplement |
| --- | --- | --- |
| 1 | KSFM | KSFM supplement |
| 2 | DMEM/F12 | KSFM supplement |
| 3 | DMEM/F12 | SHEM medium supplements without FBS |

TABLE 2

Different Culture Media for HCEC Aggregates

| Medium Type | Basal medium | Supplement |
| --- | --- | --- |
| 1 | DMEM/F12 | SHEM medium supplements |
| 2 | DMEM/F12 | SHEM medium supplements + 0.1 mg/ml BPE |
| 3 | DMEM/F12 | SHEM medium supplements + 20 ng/ml NGF |
| 4 | DMEM/F12 | SHEM medium supplements + 40 ng/ml bFGF |

Results. When incubated in a serum-containing medium, HCEC aggregates quickly attached to the plastic dish within 12 hours. In contrast, when incubated in a serum-free medium, they remained as floating aggregates (FIGS. 2C, 2G). In the latter condition, floating aggregates gradually disintegrated in a low calcium serum-free medium (Medium 1) after 1 week (FIGS. 2F, 2G).

In contrast, HCECs organized into round spheres in a high calcium serum-free medium (Medium 2 and 3) after one week (FIG. 2B) and organized into a compact round sphere for up to three weeks (FIG. 2C). At the end of the third week, these aggregates attached within 12 hours and spread out as an intact human corneal endothelial sheet within four days when seeded on plastic in SHEM (FIG. 2D). However, those preserved in a low calcium serum-free medium could only generate very few single cells (FIG. 2H). Bar represents 100 µm.

These results indicated that collagenase-isolated HCEC aggregates could be preserved for at least three weeks in a high calcium serum-free medium, and that such preserved aggregates still retained high HCEC viability for subsequent cultivation in a serum-containing medium.

Example 3

Expansion of Isolated HCEC Aggregates Using Trypsin/EDTA

The resultant HCEC aggregates, either immediately after digestion or following a period of preservation in a storage medium, were then cultured in different culture media (Table 2) on a plastic dish under a temperature of about 37° C. and five percent (5%) carbon dioxide ($CO_2$). The media were changed about every 2 to 3 days. Some HCEC aggregates were pre-treated with trypsin/EDTA at 37° C. for 10 minutes to dissociate endothelial cells before the aforementioned cultivation.

HCEC aggregates were embedded in OCT and subjected to frozen sectioning. Cryosections of 4 micrometers (µm) were air-dried at room temperature (RT) for 30 minutes, and fixed in cold acetone for 10 minutes at −20° C. Sections used for immunostaining were rehydrated in PBS, and incubated in 0.2% Triton X-100 for 10 minutes. After three rinses with PBS for 5 minutes each and preincubation with 2% BSA to block nonspecific staining, sections were incubated with anti-laminin 5, type IV collagen α1 and α2 chain, perlecan, ZO-1, and connexin 43 (all at 1:100) antibodies for one hour. After three washes with PBS for 15 minutes, the sections were incubated with a FITC-conjugated secondary antibody (goat anti-rabbit or anti-mouse IgG at 1:100) for 45 minutes.

After three additional PBS washes, each for 10 minutes, they were counterstained with propidium iodide (1:1000) or Hoechst-33342 (10 µg/mL), then mounted with an anti-fade solution and analyzed with a fluorescence microscope. HCECs cultured in 24-well plate or chamber slides were fixed in 4% paraformaldehyde for 15 minutes at RT and stained with anti-ZO-1 and connexin 43 antibodies using the above mentioned method.

For immunohistochemical staining of Ki67, endogenous peroxidase activity was blocked by 0.6% hydrogen peroxide for 10 minutes. Nonspecific staining was blocked by 1% normal goat serum for 30 minutes. Cells were then incubated with anti-Ki67 antibody (1:100) for one hour. After three washes with PBS for 15 minutes, cells were incubated with biotinylated rabbit anti-mouse IgG (1:100) for 30 minutes, followed by incubation with ABC reagent for 30 minutes. The reaction product was developed with DAB for five minutes and examined under a light microscope.

LIVE/DEAD assay and terminal deoxyribonucleotidyl transferase-mediated FITC-linked dUTP nick-end DNA labeling (TUNEL) assay were used to determine the cell viability and apoptosis, respectively. HCEC aggregates were incubated with LIVE/DEAD assay reagents for 15 minutes at room temperature. Live cells were distinguished by green fluorescence staining of the cell cytoplasm, while dead cells were stained with red fluorescence in the nuclei. TUNEL assay was performed according to the manufacturer's instructions. Briefly, cross-sections of HCEC aggregates were fixed in 4% formaldehyde for 20 minutes at RT and permeabilized with 1% Triton X-100. Samples were then incubated for 60 minutes at 37° C. with exogenous TdT and fluorescein-conjugated dUTP for repair of nicked 3'-hydroxyl DNA ends. Cells were treated with DNase I as the positive control, while the negative control was incubated with a buffer lacking rTdT enzyme. The apoptotic nuclei were labeled with green fluorescence.

Results. After brief treatment of trypsin/EDTA at 37° C. for 10 minutes, HCEC aggregates were dissociated into smaller clusters and single cells. Most cells attached and spread out within 24 hours (FIG. 5B), and grew into patches and sheets four days later. After one week, these cells reached confluence and maintained a phenotypical hexagonal shape.

Immunostaining showed confluent cells expressed the markers for maintenance of in vivo morphology: tight junction ZO-1 marker protein and gap junction connexin-43 marker protein. These results indicated that additional brief digestion by EDTA/trypsin indeed resulted in successful expansion of HCECs into a monolayer.

To further confirm that the aforementioned brief treatment of trypsin/EDTA was necessary to stimulate HCEC proliferation, we performed immunohistochemistry staining of Ki67, which is expressed at all stages of the cell cycle except G0. HCEC aggregates directly seeded on plastic without trypsin/EDTA treatment also resulted in a sheet-like growth after one week of culturing in SHEM. Nevertheless, Ki67 positive nuclei were only occasionally observed in the periphery of the growth. In contrast, following a brief trypsin/EDTA treatment, although HCEC aggregates also resulted in a confluent cell sheet if seeded on plastic in SHEM, much more cells exhibited randomly distributed Ki67-positive nuclei. This result indicated that a brief treatment of trypsin/EDTA indeed promoted cellular proliferation.

To determine whether additional supplement of growth factors in SHEM was beneficial, HCEC aggregates with or without a brief trypsin/EDTA treatment were cultured in SHEM with or without 100 μg/mL BPE, 20 ng/mL NGF or 40 ng/mL bFGF for one week. The results showed that additional BPE stimulated more scattering of cells, resulting in the loss of an intact sheet, and if pretreated with trypsin/EDTA, this phenomenon became more prominent and majority of the cells changed to a fibroblastic shape. In contrast, additional NGF did not cause the aforementioned dramatic cell shape change, and cells still maintained an intact sheet without or with trypsin/EDTA treatment. Ki67 staining revealed that addition of either BPE or NGF in SHEM yield less Ki67-positive nuclei with or without a brief treatment of trypsin/EDTA. A similar result was obtained when bFGF was added to SHEM when compared to BPE.

These results indicated that a brief trypsin/EDTA treatment resulted in more Ki67 positive cells in all of these four cultures, and that cellular proliferation was not promoted by addition of any of these three growth supplements in SHEM. Addition of BPE or bFGF in SHEM resulted in a loss of a hexagonal phenotype and cell-cell junction formation, suggesting that each of these growth supplements increased cell migration or differentiation. Overall, however, trypsin/EDTA treatment caused irreversible HCEC damage.

Example 4

Determination of mRNA Expression of Cell-Cell Junctions and their Regulatory Molecules in HCECs In Vivo and In Vitro Expression of AJs and TJs and their regulatory molecules in HCEC in vivo and in vitro, and correlation with cellular cytoskeleton actin cable and proliferation, was determined. mRNA expression of AJs/TJs and their regulatory molecules in HCEC in vivo and in vitro up to 14 days on plastic was determined by conventional reverse transcription polymerase chain reaction (RT-PCR). mRNA expression of positively expressed components of AJs in HCECs in vivo and in vitro were also determined by real-time PCR.

All PCR fragments were of the expected sizes. HCECs in vivo expressed substantial levels of mRNA of N-cadherin (type II), E-cadherin (type II), VE-cadherin, p-cadherin, p120, p190, Rac1 and RhoA, and express E-cadherin (type I), N-cadherin (type I), α-catenin, β-catenin, γ-catenin and ZO-1 at the mRNA level. HCECs in vitro, after 14 days of culture, expressed a similar level of cell-cell junction related molecules mRNA except E- (type I and II) and P-cadherin. Early recovery of N-cadherin (type II) in HCECs in vitro indicated that N-cadherin may participate in early stage of formation of AJs recruited and stabilized by p120. At this stage, p120 may spread into cytosol and nucleus, and act as a transcriptional factor. N-cadherins may spread from junction to cytosol as the signs of immaturation. At day 21, N-cadherin formed circular bands at the cell-cell junction, and p-120 formed circular bands at the inner cell membrane while N-cadherin and VE-cadherin were in cytosol of HCECs. This pattern represents a mature pattern resembling what is found in vivo.

A brief treatment of Trypsin/EDTA markedly dissociated AJ and TJ components as evidenced by significant downregulation of VE-cadherin, N-cadherin (type II), β-catenin and ZO-1 the least (Table 3). In this case, AJs and TJs were not or poorly formed within 2 days of culture.

Slides of flat mount of human endothelial Descemet's membrane were prepared, air-dried at room temperature, and immediately fixed in 4% formaldehyde at room temperature. Sections used for immunostaining were rehydrated in PBS, and incubated in 0.2% Triton X-100 for 15 minutes. After three rinses with PBS for 5 minutes each and preincubation with 2% BSA to block nonspecific staining from 30 min, the sections were incubated with anti-N-cadherin, E-cadherin, VE-cadherin and p120 (all at 1:50) antibodies for 16 hours at 4 C. After three washes with PBS for 15 minutes, the sections were incubated with a Texas-red conjugated secondary antibody (donkey anti-rabbit or anti-mouse IgG at 1:100) for 60 minutes. After three additional PBS washes, each for 10 minutes, they were counterstained with Hoechst 33342 (10 μg/mL), then mounted with an antifade solution and analyzed with a fluorescence microscope.

Results. HCEC cultured in vitro had elevated levels of p120, p190 and β-catenin after 14 days of culture. Levels of p120 for HCEC in vitro were four times higher than HCEC in vivo, which may prohibit HCEC proliferation in vitro. Real-time PCR results were comparable with those from RT-PCR.

TABLE 3

Summary of mRNA expression of AJ-related molecules.

| Day of Culture | Expression of Catenin mRNAs | | | | VE-cad | Expression of Cadherin mRNAs | | | | P-cad | Other AJs Regulatory Molecule mRNAs | | |
| --- | --- | --- | --- | --- | --- | --- | --- | --- | --- | --- | --- | --- | --- |
| | | | | | | E-cad | | N-cad | | | | | |
| | α-cat | β-cat | γ-cat | P120 | | Type 1 | Type 2 | Type 1 | Type T 2 | | p190 | Rac1 | RhoA |
| 0 | ++ | +++ | ++ | ++ | ++ | + | ++ | + | ++ | + | + | ++ | +++ |
| 2+ T/EDTA | --- | --- | --- | ++ | --- | --- | --- | --- | --- | --- | --- | + | + |
| 2- T/EDTA | --- | + | --- | ++ | ++ | --- | --- | --- | ++ | --- | --- | ++ | + |
| 14- T/EDTA | ++ | +++ | ++ | +++ | +++ | --- | --- | + | ++ | --- | + | +++ | +++ |

TABLE 4

Real-time PCR results from in vitro HCEC compared with in vivo samples

| Fold of Increase | Expression of Catenin mRNAs | | E-cadherin | VE-cadherin (endothelial) | Expression of p190RhoGAP mRNAs |
|---|---|---|---|---|---|
| | p120 | β-catenin | | | p190 |
| In vivo | 1 | 1 | 1 | 1 | 1 |
| 2-day culture, trypsin-EDTA | 0.5, 0.63 | 1.1, 1.3 | 0, 0 | 0, 0 | 0, 0 |
| 2-day culture | 4.2, 3.4 | 12.8, 7.2 | 0 | 1.2, 0.8 | 0, 0 |
| 14-day culture | 3.8, 3.8 | 6.5, 3.8 | 0 | 0.7, 1.4 | 1.7, 2.1 |

N-cadherin and p120 levels were also correlated with the maturation of cytoskeletons (actin cable formation) in cultured HCEC at day 7, 14 and 21 by immunostaining, indicating that their expression are correlated with in vitro maturation of AJs and stabilization of AJs at late confluence.

First, N-, E-, VE-cadherin, p120 and actin cytoskeleton cables were identified in HCEC in vivo by flat mount preparation of Descemet's membrane with endothelial cells. HCEC in vivo displayed circular N-cadherin bands mainly at the cell-cell borders, continuous circular E-cadherin bands mostly in cytosol, and weak, discontinuous circular VE-cadherin bands in cytosol. P120 was arranged in cytosol close to the cell-cell border in HCEC in vivo, forming a circular band. F-actin was arranged into dense peripheral bands (DPB) in individual cells that are separated from those in adjacent cells.

Next, the staining pattern of N-cadherins, p120 and actin cytoskeleton cables were identified in HCEC in vitro, and N-cadherin staining was correlated with proliferation by BrdU labeling, to determine when circular N-cadherins in HCECs could be determined in vitro and whether N-cadherins correlated with cell mitotic block. HCEC in vitro without first antibody were used as negative control.

Results. HCEC in vitro at day 21 displayed circular N-cadherin bands mainly at the cell-cell borders, similar to the localization and staining pattern of HCEC in vivo, indicating maturation of HCEC in vitro. HCEC in vitro at day 7 already formed broken circular bands, and HCEC in vitro at day 14 still displayed incomplete circular bands of N-cadherin at the cell-cell junctions, indicating the HCEC at these stages of culture were immature. P120 was arranged in inner cell membrane in HCEC in vitro at day 21, with a circular band, indicating the HCEC were mature. At day 7 and 14, p120 was mainly in cytosol of HCEC in vitro, indicating those cells were still immature. BrdU labeling indicated that the HCEC proliferation rate at day 7 of culture was 40 times higher than that at day 21.

Example 5

Transient Downregulation of p120 by RNAi Knockdown in ARPE-19 Cell Line

Materials. Dulbecco's modified Eagle's medium (DMEM), Ham's/F12 medium, human epidermal growth factor (hEGF), HEPES buffer, Hanks' balanced salt solution (HBSS), phosphate-buffered saline (PBS), amphotericin B, gentamicin, fetal bovine serum (FBS), and 0.25% trypsin/0.53 mM EDTA (trypsin/EDTA) were purchased from Invitrogen (Carlsbad, Calif.). Collagenase A was obtained from Roche (Indianapolis, Ind.). Hydrocortisone, dimethyl sulfoxide, cholera toxin, and insulin-transferrin-sodium selenite media supplement were purchased from Sigma-Aldrich (St. Louis, Mo.). ARPE-1 g cell line was purchase from ATCC (Manassas, Va.). GeneEraser™ siRNA transfection reagent was purchased from Stratagene (La Jolla, Calif.). RNAeasy Mini kit was obtained from Qiagen (Valencia, Calif.). High Capacity Reverse Transcription Kits and Real-time PCR primers and probes were ordered from Applied Biosystems (Foster City, Calif.). Monoclonal anti-VE-cadherin and polyclonal anti-E-cadherin, anti-N-cadherin and p120 antibodies were obtained from Santa Cruz (Santa Cruz, Calif.). Texas-red conjugated donkey anti-rabbit or mouse were from Jackson ImmunoResearch (West Grove, Pa.). FITC conjugated goat anti-rabbit antibody was from Sigma-Aldrich.

ARPE-19 cells were cultured in DMEM/F12 (1:1) plus 10% FBS. The cells were cultured until early (4 days) and late confluence (4 weeks, FIG. 3).

RNAi was chosen following the RNAi design principles published in Mittal V, *Nature* (2004) 5:355-365. Invitrogen Blockit™ RNAi Designer was used to design two more p120-specific RNAi sequences in addition to the two RNAi sequences published in Davis M A, Ireton R C, Reynolds A B, *J Cell Biol*. (2003) Nov. 10; 163(3):525-34. A BLAST search was conducted to ensure that the RNAi sequences chosen were p120-specific. RNAi targeted sequences are listed in Table 5.

TABLE 5

Targeted RNAi Sequences

```
RNAi 1 P120 RNAi 1, published, sense
       5'GCCAGAGGTGGTTCGGATA3'    (SEQ ID NO.: 1)
       P120 RNAi 1, published, antisense
       5'TATCCGAACCACCTCTGGC3'    (SEQ ID NO.: 2)

RNAi 2 P120 RNAi 2, published, sense
       5'AACGAGGTTATCGCTGAGAAC3'  (SEQ ID NO.: 3)
       P120 RNAi 2, published, antisense
       5'GTTCTCAGCGATAACCTCGTT3'  (SEQ ID NO.: 4)

RNAi 3 P120 RNAi 3, sense
       5'CAGAGGTGATCGCCATGCTTGGATT3'  (SEQ ID NO.: 5)
       P120 RNAi 3, antisense
       5'AATCCAAGCATGGCGATCACCTCTG3'  (SEQ ID NO.: 6)

RNAi 4 P120 RNAi 4, sense
       5'GCGATTGCTTCGAAAGGCTCGTGAT3'  (SEQ ID NO.: 7)
       P120 RNAi 4, antisense
       5'ATCACGAGCCTTTCGAAGCAATCGC3'  (SEQ ID NO.: 8)
```

Fifty μl of sterile, room temperature, serum-free, antibiotic-free DMEM/F12 medium was transferred to a polystyrene tube, and was added with 3 μl of GeneEraser siRNA transfection reagent into the serum-free medium. After mixing thoroughly by vortexing, it was then incubated at room temperature for 15 minutes. This mixture was then added with 3.0 μl of 1-μM p120 siRNA sample, mixed gently by pipetting, and incubated at room temperature for 15 minutes. The final transfection mixture was added dropwise to a well of 24-well dish with the cells cultured in 250 μl fresh serum-containing medium, and the culture was cultured for 48 hours in the incubator before subjecting to RNA extraction and real-time PCR.

Figure 3:
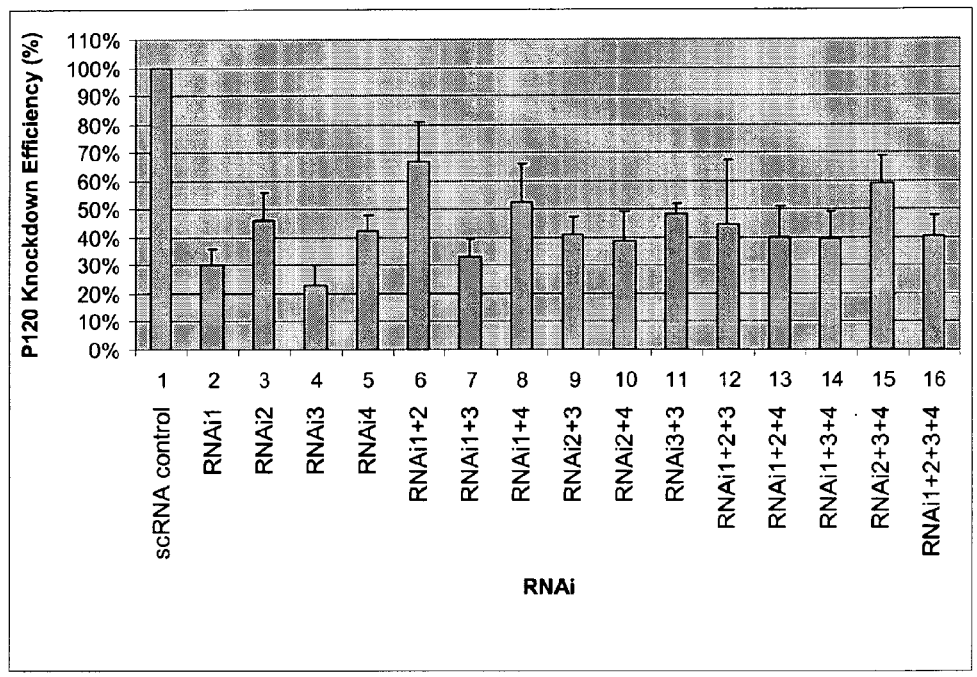
FIG. 3 is an illustrative graph showing RNAi knockdown efficiency by real-time PCR quantitation of p120 mRNA using ARPE-19 cell line, Late Confluent (4 week culture).

Results. P120 RNAi 1 and 3 were most effective. No synergistic action between RNAi 1 and 3 was seen. Efficiency of knockdown was as high as 90-95% using early confluent ARPE-19 cells; and combinations of p120 RNAi did not enhance the efficiency due to so call "off-target effect." Efficiency of knockdown was lower (as high as 70-75%) using late confluent ARPE-19 cells (FIG. 3). After p120 knockdown, E- and VE-cadherin was lost, and p190 was downregulated (Table 6).

TABLE 6 mRNA expression after P120 RNAi knockdown in ARPE-19 cells (real-time PCR)

| Fold of Increase | Expression of Catenin mRNAs | | Expression of Cadherin mRNAs | | Expression of p190RhoGAP |
| --- | --- | --- | --- | --- | --- |
| | p120 | β-catenin | E-cadherin | VE-cadherin (endothelial) | mRNAs p190 |
| Control | 1 | 1 | 1 | 1 | 1 |
| P120 knockdown1 | 0.08, 0.07 | 0.8, 1.0 | 0, 0 | 0, 0 | 0.4, 0.4 |
| P120 knockdown2 | 0.05, 0.06 | 1.6, 0.9 | 0, 0 | 0, 0 | 0.5, 0.5 |

Example 6

Transient Downregulation of p120 by RNAi Knockdown in HCEC

Human tissue was handled according to the Declaration of Helsinki. Eight corneoscleral tissues from human donor eyes were obtained from the Florida Lions Eye Bank (Miami, Fla.). Some of their central corneal buttons had been used for corneal transplantation. The donors' ages were between 3 to 65 years old. All tissues were maintained at 4° C. in storage medium (Optisol; Chiron Vision, Irvine, Calif.) for less than 10 days before study. The tissue was rinsed three times with DMEM containing 50 mg/mL gentamicin and 1.25 mg/mL amphotericin B. The central cornea was removed by a trephine of 8-mm diameter. Afterward, the Descemet's membrane and corneal endothelial cells were stripped from the posterior surface of the peripheral corneoscleral tissue under a dissecting microscope and digested at 37° C. for 16 hours with 1 mg/mL collagenase A in supplemented hormonal epithelial medium (SHEM), which was made of an equal volume of HEPES-buffered DMEM and Ham's F12 supplemented with 5% FBS, 0.5% dimethyl sulfoxide, 2 ng/mL mouse EGF, 5 μg/mL insulin, 5 μg/mL transferrin, 5 ng/mL selenium, 0.5 μg/mL hydrocortisone, 1 nM cholera toxin, 50 μg/mL gentamicin, and 1.25 μg/mL amphotericin B. After digestion, HCECs formed aggregates, which were collected by centrifugation at 2000 rpm for 3 minutes to remove the digestion solution. The aggregates were cultured for 3 and 14 days in SHEM medium.

RNAs from HCECs in vivo or in vitro aggregates/patches were lysed and extracted using RNAeasy Mini kit (Qiagen). The extracted RNA was reverse-transcribed using High Capacity Reverse Transcription Kit (Appliedbiosystems). Amplification of AJ components was performed by PCR using specific primers and DNA polymerase (Appliedbiosystems). The PCR profile consisted of 6 minutes of initial denaturation at 95° C. followed by 35 cycles of 30 sec denaturation at 95° C., 1 min annealing at 60° C. and 1 min extension at 72° C. For real-time PCR, it consisted of 10 minutes of initial denaturation at 95° C. followed by 40 cycles of 30 sec denaturation at 95° C., 1 min annealing and extension at 60° C.

P120 knockdown experiments were performed at day 21 when E-cadherin mRNA appeared, indicating that AJs were mature and the cells were not proliferating. Fifty μl of sterile, room temperature, serum-free, antibiotic-free DMEM/F12 medium was transferred to a polystyrene tube, and was added with 3 μl of GeneEraser siRNA transfection reagent into the serum-free medium. After mixing thoroughly by vortexing, it was then incubated at room temperature for 15 minutes. This mixture was then added with 3.0 μl of 1-μM p120 siRNA sample, mixed gently by pipetting, and incubated at room temperature for 15 minutes. The final transfection mixture was added dropwise to a well of 24-well dish with the cells cultured in 250 μl fresh serum-containing medium, and the culture was cultured for 48 hours in the incubator before subjecting to RNA extraction and real-time PCR to examine the mRNA changes of p120, p190, E-, vE-, N-cadherins, and β-catenin. Double-immunostaining/immunohistochemistry with p120, N-cadherin, and BrdU antibodies with Scramble RNAi-treated samples were used as controls.

Results. P120 knockdown in HCECs cultured in vitro for 3 weeks resulted in dramatic downregulation of p120, E- and VE-cadherin, moderate reduction of p190, and no significant change of β-catenin (Tables 7 and 8). Additionally, p120 was translocalized to the nucleus of the cells which showed cellular proliferation as judged by nuclear staining of BrdU (FIG. 4).

TABLE 7 mRNA expression after P120 RNAi knockdown in HCEC 3 week culture (real-time PCR)

| Fold of Increase | Expression of Catenin mRNAs | | Expression of Cadherin mRNAs | | Expression of p190RhoGAP |
| --- | --- | --- | --- | --- | --- |
| | p120 | β-catenin | E-cadherin | VE-cadherin (endothelial) | mRNAs p190 |
| Control | 1 | 1 | 1 | 1 | 1 |
| P120 knockdown1 | 0.119, 0.102 | 0.702, 0.852 | 0.192, 0.183 | 0.035, 0.051 | 0.334, 0.292 |
| P120 knockdown2 | 0.199, 0.153 | 0.755, 0.823 | 0.175, 0.161 | 0.077, 0.061 | 0.244, 0.215 |

TABLE 8

Molecule changes after p120 knockdown.

| Cell type | P120 | P190 | VE-cadherin | N-cadherin (II) | E-cadherin (I) | β-catenin | RhoA | Rac1 |
| --- | --- | --- | --- | --- | --- | --- | --- | --- |
| Cells in mitotic block | +++ | +++ | +++ | +++ | ++ | +++ | + | +++ |
| P120 knockdown | --- | + | --- | --- | --- | + | +++ | + |

While this invention has been particularly shown and described with references to the disclosed embodiments thereof, it will be understood by those skilled in the art that various changes in form and details may be made therein without departing from the scope of the invention encompassed by the appended claims.

What is claimed is:

1. A method of stimulating the proliferation of a plurality of endothelial cells or epithelial cells with adherent junctions in vivo, comprising transiently contacting a plurality of endothelial cells or epithelial cells with adherent junctions in an eye of a mammal with an agent that downregulates expression of E-cadherin, VE-cadherin, P-cadherin, N-cadherin, α-catenin, β-catenin, p120 catenin, p190, or any combination thereof; wherein the agent is an agent that induces RNAi, thereby stimulating the proliferation of the plurality of cells.

2. The method of claim 1, comprising downregulating the expression of p120 catenin.

3. The method of claim 1, wherein the contacting occurs in pulses that are followed by withdrawal of the agent that induces RNAi.

4. The method of claim 1, wherein the pulse of the agent that induces RNAi is administered for at least 12 hours.

5. The method of claim 1, wherein the mammal has a corneal endothelial dysfunction.

6. The method of claim 1, comprising administering the agent to an anterior chamber of the eye of the mammal.

7. The method of claim 1, wherein the plurality of endothelial cells or epithelial cells with adherent junctions are human corneal epithelial cells.

8. A method of generating an expanding monolayer of human corneal endothelial cells in culture, comprising: (a) transiently contacting an aggregate or monolayer of human corneal endothelial cells with an RNAi-inducing agent that downregulates expression of N-cadherin, α-catenin, β-catenin, p120 catenin, p190, or any combination thereof, to generate expandable human corneal epithelial cells; and (b) culturing the expandable human corneal endothelial cells in media free of Cholera toxin and bFGF, such that they form an expanding monolayer of human corneal endothelial cells.

9. The method of claim 8, comprising downregulating the expression of p120 catenin.

10. The method of claim 8, wherein the contacting occurs in pulses that are followed by withdrawal of the RNAi-inducing agent.

11. The method of claim 10, wherein the pulse of the RNAi-inducing agent is administered for at least 12 hours.

12. The method of claim 8, wherein the human corneal endothelial cells are in early or late confluence.

13. The method of claim 4, wherein the pulse of the agent that induces RNAi is administered daily, three times a week, twice a week, or weekly.

14. The method of claim 8, further comprising contacting the cells with a mitogenic growth factor, an agent that elevates intracytoplasmic cAMP, or a combination thereof.

15. The method of claim 8, wherein a pulse of an agent that induces RNAi is administered daily, three times a week, twice a week, or weekly.

16. The method of claim 8, wherein the expanded aggregate or monolayer of human corneal endothelial cells is used to make a surgical graft.

17. The method of claim 1, wherein the plurality of endothelial cells or epithelial cells with adherent junctions are human corneal endothelial cells.

18. The method of claim 1, further comprising contacting the cells with a mitogenic growth factor, an agent that elevates intracytoplasmic cAMP, or a combination thereof.

19. The method of claim 18, wherein the agent that elevates intracytoplasmic cAMP is selected from 8-bromo-cAMP, dibutyryl cAMP, isobutylmethylxanthine, Pentoxifylline, forskolin, cholera toxin, prostaglandin E2 (PGE2), phenylbutyrate, Butaprost, or Iloprost.

20. The method of claim 14, wherein the agent that elevates intracytoplasmic cAMP is selected from 8-bromo-cAMP, dibutyryl cAMP, isobutylmethylxanthine, Pentoxifylline, forskolin, cholera toxin, prostaglandin E2 (PGE2), phenylbutyrate, Butaprost, or Iloprost.

* * * * *